(12) United States Patent  
Cardelius

(10) Patent No.: US 6,691,552 B2
(45) Date of Patent: Feb. 17, 2004

(54) METHOD AND APPARATUS FOR MONITORING THE COMPOSITION OF A BINARY BREATHING GAS MIXTURE

(75) Inventor: Erik Cardelius, Stockholm (SE)

(73) Assignee: Siemens Elema AB, Sölna (SE)

( * ) Notice: Subject to any disclaimer, the term of this patent is extended or adjusted under 35 U.S.C. 154(b) by 0 days.

(21) Appl. No.: 10/408,922

(22) Filed: Apr. 8, 2003

(65) Prior Publication Data

US 2003/0217583 A1 Nov. 27, 2003

(30) Foreign Application Priority Data

May 23, 2002 (SE) .............................. 0201541

(51) Int. Cl.[7] .......................... G01N 19/10; G01N 7/00; A61M 16/00
(52) U.S. Cl. .................. 73/23.2; 73/31.06; 128/204.21
(58) Field of Search ................ 73/23.2, 23.3, 73/23.42, 31.06, 335.08, 861.04; 128/204.21

(56) References Cited

U.S. PATENT DOCUMENTS

| 4,509,359 A | * | 4/1985 | Gedeon et al. | ............... 73/23.3 |
| 5,485,754 A | * | 1/1996 | Harpster | .................. 73/861.04 |
| 5,823,186 A | | 10/1998 | Rossen et al. | |
| 5,850,833 A | | 12/1998 | Kotliar | |
| 6,038,922 A | * | 3/2000 | Mauze et al. | ............. 73/335.08 |
| 6,128,945 A | * | 10/2000 | Shioiri et al. | ............... 73/31.06 |
| 6,138,674 A | * | 10/2000 | Gull et al. | ............. 128/204.21 |
| 6,490,910 B1 | * | 12/2002 | Butler et al. | ................ 73/23.42 |
| 2002/0047311 A1 | * | 4/2002 | Hugh | ......................... 307/116 |

FOREIGN PATENT DOCUMENTS

| EP | 0 512 285 | 11/1992 |
| EP | 0 860 175 | 8/1998 |
| WO | WO 98/44976 | 10/1998 |

* cited by examiner

Primary Examiner—Hezron Williams
Assistant Examiner—Jay L Politzer
(74) Attorney, Agent, or Firm—Schiff Hardin & Waite

(57) ABSTRACT

In a method and apparatus for monitoring the composition of a breathing gas mixture having a first gaseous component and a second gaseous component, a data processor is supplied, either as an input value or as a measured value from associated humidity sensors with an indication of a moisture content value ($RH_{Comp1}$) for the first gaseous component and a moisture content value ($RH_{Comp2}$) second gaseous component before mixing. An indication of the moisture content value for the mixture ($RH_{Mix}$) is measured and provided to the data processor. From these inputs the data processor determines a value indicative of the amount (x,y) of one or both of the first gaseous component and the second gaseous component in the mixture according to the relationship: $RH_{Comp1} \cdot x + RH_{Comp2} \cdot y = RH_{Mix}$.

9 Claims, 1 Drawing Sheet

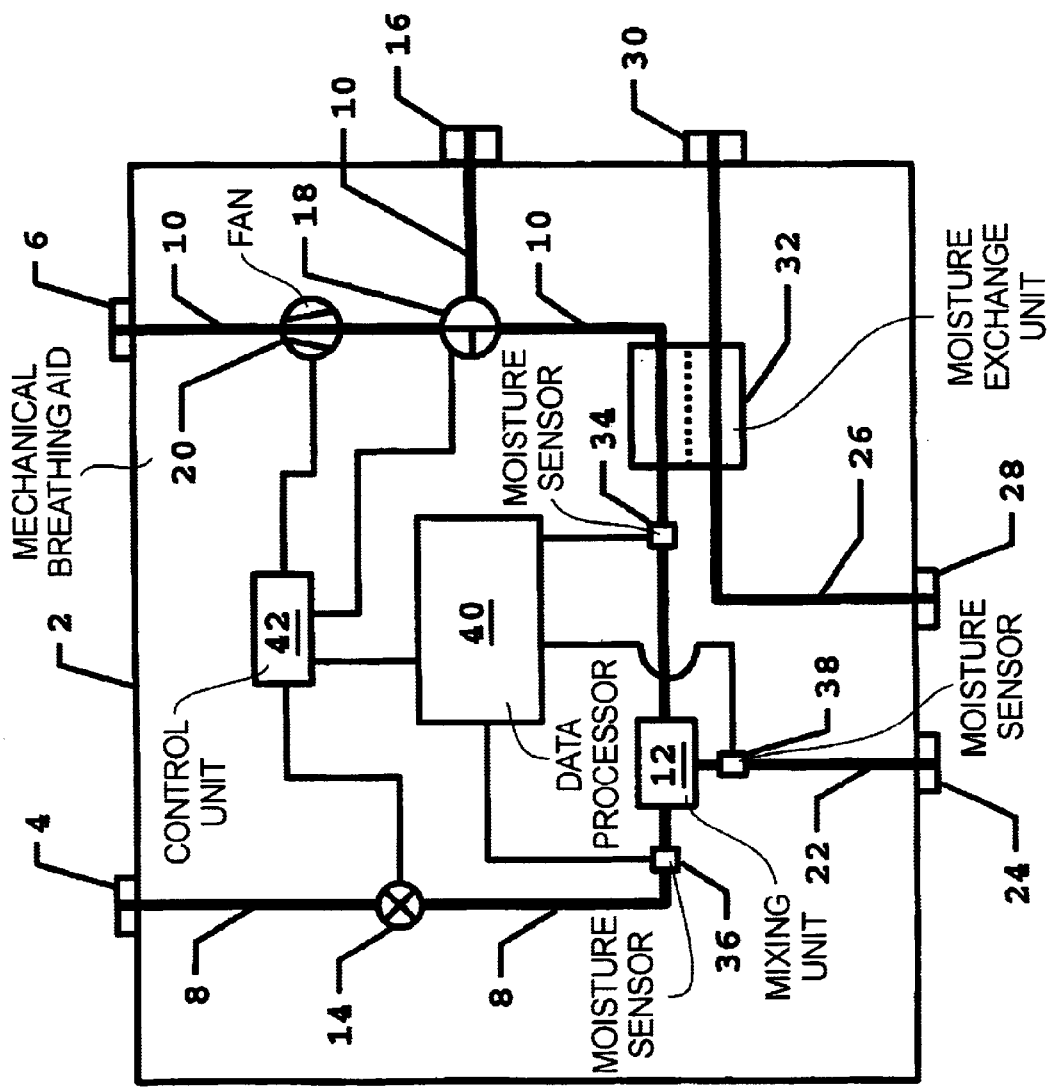

METHOD AND APPARATUS FOR MONITORING THE COMPOSITION OF A BINARY BREATHING GAS MIXTURE

BACKGROUND OF THE INVENTION

1. Field of the Invention

The present invention relates to a method and an apparatus for monitoring the composition of a binary (two-component) breathing gas mixture, in particular an air-oxygen mixture, intended for supply by a mechanical breathing aid, such as a patient ventilator or an inhalation anesthetic delivery system.

2. Description of the Prior Art

It is known to provide a mechanical breathing aid that is devised for supplying a mixture of gases, such as an oxygen-enriched air mixture or a mixture of nitrous oxide ($N_2O$) in a breathable gas, to a patient as a breathing gas. For this purpose the breathing aid is provided with an inlet for a first component, such as air or other breathable gas, of the breathing gas mixture. This first component may be drawn into the breathing aid from the atmosphere or may be provided from a pressurized source. The breathing aid also is provided with an inlet for a second component, such as oxygen or $N_2O$, of the binary mixture, typically from a pressurized source, and an outlet for a breathing gas mixture. Automatic flow control valves are often associated with one or both of the inlets and are operable to adjust the gas flow there through dependent on a measured air-oxygen mixture and a desired air-oxygen mixture of the breathing gas. A gas sensor is located in gaseous communication with the mixture to monitor the level of one or the other of the components in the mixture, such as monitoring the oxygen level, and to provide an output indicative thereof. A controller usually is provided and is arranged in operative connection to the sensor and to the valves to vary the flow through the associated inlet in response to the sensor output. The gas sensor is typically a chemical sensor, which has a rather limited lifetime as compared with the expected lifetime of the mechanical breathing aid. Although a type of gas sensor is available that is responsive to the paramagnetic properties of component to be monitored, for example oxygen, which does not have the limited lifetime of the chemical sensor, however, this type of sensor is generally expensive and is sensitive to mechanical vibrations that are present in most mechanical breathing aids.

SUMMARY OF THE INVENTION

It is an object of the present invention to provide a method and an apparatus for determining the composition of a binary component breathing gas that avoids or at least alleviates the aforementioned problems associated with known methods and devices of this type.

This object is achieved in accordance with the principles of the present invention in a method and an apparatus for monitoring the composition of a breathing gas containing a first gaseous component and a second gaseous component, wherein a data processor is supplied with an indication of the moisture content of the first gaseous component before mixing with the second gaseous component, and wherein the data processor also is supplied with an indication of the moisture content of the second gaseous component before mixing with the first gaseous component. A moisture content value for the mixture is then measured and supplied to the data processor. Using this input, the data processor determines a value indicative of the amount of one or both of the first gaseous component and the second gaseous component in the mixture.

The amounts of one or both of the two components are determined indirectly through the comparison of levels of humidity in the gaseous components and in the mixture. This allows for a relatively robust and inexpensive humidity sensor to be substituted for the gas sensor conventionally employed.

Moisture may be added to one of the gas components to provide a significant difference in moisture content between the two components and thereby enhance the accuracy of the method.

Preferably, the moisture may be added to achieve a predetermined level of humidity in the selected gas component. The humidity sensor associated with the monitoring of humidity levels in the selected gas component may then be omitted and a value of the predetermined humidity level provided directly.

DESCRIPTION OF THE DRAWINGS

The FIGURE is a schematic representation of a mechanical breathing aid incorporating a monitoring apparatus constructed and operating according to the present invention.

DESCRIPTION OF THE PREFERRED EMBODIMENTS

The FIGURE figure schematically illustrates a mechanical breathing aid 2, such as a patient ventilator. Some of breathing aid 2 is of a generally known construction and so only those elements which depart from conventional components and which are necessary for an understanding of the invention will be described.

The breathing aid 2 is provided with an inlet 4 for, in the present example, oxygen and an inlet 6 for, in the present example, ambient air. It will be appreciated that other gaseous components of a breathing gas may substitute for or be provided in addition to the air and oxygen of the present embodiment without departing from the invention.

Conduits 8,10 are connected respectively to the inlets 4,6 and define internal flow paths within the breathing aid 2 for oxygen and air, respectively. The conduit 8 connects the oxygen inlet 4 to a mixing unit 12 via an automatic flow control valve 14, which may be a part of the mixing unit 12. The conduit 10 connects the air inlet 6 to the mixing unit 12 and, in the present example, to an outlet 16. A two-way valve 18 in the conduit 10 may be automatically operated to selectively connect either the mixing unit 12 or the air outlet 16 to the air inlet 6. In the present embodiment a fan 20 is located in communication with the conduit 10 and operates to draw in air through the inlet 6 from the exterior of the breathing aid 2. Alternatively, other means to draw in air, such as a pump, may be provided, or the inlet 6 may be connected to an external source of pressurized air.

In the present example the fan 20 operates continuously throughout a breathing cycle of a patient and the two-way valve 18 is operable to divert airflow to the outlet 16 during an expiration phase of the patient breathing cycle. A conduit 22 provides an internal flow path for gas from the mixing unit 12 to an outlet 24 that in use will connect to an inspiration side of a patient tubing circuit (not shown) for onward transmission to the airways of a patient. A further conduit 26 connects an inlet 28, which in use will connect to the expiration side of the patient tubing circuit, to an outlet 30. The conduit 26 is also connected to a moisture exchange unit 32, as is the conduit 10 for the air. The moisture exchange unit 32 operates in a known manner to extract moisture from expiration gas flowing therethrough from the conduit 26, and to provide moisture to through flowing inspiration gas from the conduit 10. Other known humidifiers may substitute for the exchange unit 32, such as a humidifier that operates to introduce an amount of water vapor into air within the conduit 10 to establish a predetermined relative humidity level for the air passing from the conduit 10 and into the mixing unit 12.

As an alternative, moisture may be introduced into the oxygen and substantially dry air supplied into the mixing unit 12. It is important that the difference in humidity between the two components is sufficiently large so as to avoid substantial errors being made in the calculations detailed below. It is therefore preferable if one of the components supplied to the mixing unit 12 is essentially free of moisture.

Since the moisture content of the air within the conduit 10 that exits from the moisture exchange unit 32 is unknown, a moisture sensor 34, such as is commercially available from Honeywell and operates to monitor changes in electrical capacitance, is provided to establish a relative humidity value for the air at a location between the moisture exchanger 32 and the mixing unit 12. Similar sensors 36,38 are provided to establish a relative humidity value for the oxygen (sensor 36) and for the oxygen-air mixture (sensor 38). If the relative humidity of one or both of the air and the oxygen is known then the associated sensor may be omitted.

The respective outputs from the sensors 34, 36, 38, indicating the relative humidity level in air, oxygen and the oxygen-air mixture respectively within the breathing aid 2, is provided to a data processor 40, which may be a microcomputer programmed using standard programming techniques. It will be appreciated that if the humidity level of one or both of the air in the conduit 10 and the oxygen in the conduit 8 is fixed, for example zero, then the value of the relative humidity level for the gas in which it is fixed can be entered into the data processor 40 in a number of standard ways. The value, for example, can be pre-loaded into a memory device within the data processor 40 or can be entered by a user using a data entry device (not shown), such as a keyboard or touch screen, operably connected to the data processor 40.

The data processor 40 is programmed to calculate, in the present example, the percentage of oxygen added to the air according to the following equation:

$$RH_{O_2} \cdot x + RH_{Air} \cdot y = RH_{Mix} \quad (1)$$

where $RH_{O2}$ is the relative humidity value for the added oxygen; $RH_{Air}$ is the relative humidity value for air; and $RH_{Mix}$ is the relative humidity value for the oxygen-air mixture.
x and y are the fractions of added oxygen and air respectively so that:

$$x+y=1 \quad (2)$$

and $$x = \frac{RH_{Mix} - RH_{Air}}{RH_{O_2} - RH_{Air}} \quad (3)$$

Since air already contains about 20.9% oxygen then the percentage of total oxygen, $\%O_2$, in air may be calculated according to:

$$\%O_2 = (x + y \cdot 0.209) \cdot 100 \quad (4)$$

A signal dependent on the calculated percentage is output from the data processor 40 and, in the present example, is supplied to a control unit 42 where it is employed in the generation of a control signal usable to regulate the relative proportions of oxygen and air that pass from the associated conduits 8,10 into the mixing unit 12. Additionally or alternatively, a humanly perceptible alarm (not shown) may be operated if the percentage calculated in this manner indicates a deviation from an expected value. In the present example the control unit 42 is configured to automatically adjust the flow control valve 14 associated with the oxygen conduit 8 in order to regulate the oxygen flow into the mixing unit 12 and thereby achieve a desired mixture.

It will be appreciated that the above equations (1–3) can be generalized and applied to calculate the composition of any two component ($Comp_1$ and $Comp_2$) breathing gas mixture (Mix) as:

$$RH_{Comp_1} \cdot x + RH_{Comp_2} \cdot y = RH_{Mix} \quad (5)$$

$$x+y=1 \quad (6)$$

and $$x = \frac{RH_{Mix} - RH_{Comp_2}}{RH_{Comp_1} - RH_{Comp_2}} \quad (7)$$

It will be further appreciated that one or both of the component gases $Comp_1$, $Comp_2$ may themselves be a multi-component mixture and can either be supplied directly to an inlet of the breathing aid or created within the breathing aid from component gases supplied to an associated inlet. Moreover, the mixture of the two component gases $Comp_1$, $Comp_2$, may itself form a component of a further binary mixture, the composition of which may be monitored using the method and apparatus of the present invention.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for monitoring a composition of a breathing gas mixture comprising a first gaseous component and a second gaseous component, comprising the steps of:
   providing a data processor with an indication of a moisture content value for said first gaseous component before mixing thereof with said second gaseous component;
   providing said data processor with an indication of a moisture content value for said second gaseous component before mixing thereof with said first gaseous component;
   after mixing said first gaseous component and said second gaseous component to obtain a mixture, measuring a moisture content value for said mixture and providing said moisture content value for said mixture to said data processor; and
   determining, in said data processor, a value indicative of an amount of one or both of said first gaseous component and said second gaseous component in said mixture, from said moisture content value for said first gaseous component, said moisture content value for said second gaseous component, and said moisture content value for said mixture.

2. A method as claimed in claim 1 comprising the additional step of introducing moisture into one of said first gaseous component in said second gaseous component.

3. A method as claimed in claim 2 comprising introducing said moisture to achieve a predetermined moisture level in said one of said first gaseous component and said second gaseous component.

4. A monitoring apparatus for monitoring a composition of a breathing gas mixture comprising a first gaseous component and a second gaseous component, said monitoring apparatus comprising:

a data processor;

a first arrangement operable to obtain and make accessible to said data processor a moisture content value for said first gaseous component before mixing thereof with said second gaseous component;

a second arrangement operable to obtain and make accessible to said data processor a moisture content value for said second gaseous component before mixing thereof with said first gaseous component;

a sensor operable to measure and make accessible to said data processor a moisture content value for a mixture of said first gaseous component and said second gaseous component; and said data processor, from said moisture content value for said first gaseous component, said moisture content value for said second gaseous component, and said moisture content value for said mixture, being configured to determine a value indicative of an amount of one or both of said first gaseous component and said second gaseous component in said mixture, and to generate an output representing said amount.

5. A monitoring apparatus as claimed in claim 4 comprising a humidifier disposed to interact with said first gaseous component to introduce moisture in said first gaseous component.

6. A monitoring apparatus as claimed in claim 4 comprising a humidifier disposed to interact with said second gaseous component to introduce moisture in said second gaseous component.

7. A monitoring apparatus as claimed in claim 4 wherein said first arrangement comprises a moisture sensor.

8. A monitoring apparatus as claimed in claim 4 wherein said second arrangement comprises a moisture sensor.

9. A monitoring apparatus as claimed in claim 4 wherein said first arrangement comprises a first moisture sensor and wherein said second arrangement comprises a second moisture sensor.

* * * * *